United States Patent
Rogers et al.

(10) Patent No.: US 9,271,689 B2
(45) Date of Patent: Mar. 1, 2016

(54) APPARATUS FOR WIDE COVERAGE COMPUTED TOMOGRAPHY AND METHOD OF CONSTRUCTING SAME

(75) Inventors: Carey Shawn Rogers, Brookfield, WI (US); Richard Michael Roffers, Menomonee Falls, WI (US); Edwin L. Legall, Menomenee Falls, WI (US); Ron Kent Hockersmith, Waukesha, WI (US); Ethan Westcot, Wauwatosa, WI (US); Kenwood Dayton, Mequon, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 12/690,173

(22) Filed: Jan. 20, 2010

(65) Prior Publication Data

US 2011/0176659 A1 Jul. 21, 2011

(51) Int. Cl.
*H01J 35/10* (2006.01)
*A61B 6/00* (2006.01)
*A61B 6/03* (2006.01)

(52) U.S. Cl.
CPC .......... *A61B 6/482* (2013.01); *A61B 6/032* (2013.01); *A61B 6/405* (2013.01); *A61B 6/4007* (2013.01); *A61B 6/4014* (2013.01); *A61B 6/4241* (2013.01); *A61B 6/035* (2013.01); *A61B 6/4085* (2013.01); *Y10T 29/49002* (2015.01)

(58) Field of Classification Search
CPC ....................................................... H01J 35/08
See application file for complete search history.

(56) References Cited

U.S. PATENT DOCUMENTS

| | | | |
|---|---|---|---|
| 3,942,059 A * | 3/1976 | Tran-Quang | 378/128 |
| 4,129,783 A | 12/1978 | Houston | |
| 4,150,293 A | 4/1979 | Franke | |
| 4,153,842 A | 5/1979 | Rohmfeld | |
| 4,196,352 A | 4/1980 | Berninger et al. | |
| 4,203,036 A | 5/1980 | Tschunt | |
| 4,274,005 A | 6/1981 | Yamamura et al. | |
| 4,303,830 A | 12/1981 | Heinzelmann et al. | |
| 4,345,158 A | 8/1982 | Pfeiler et al. | |
| 4,347,624 A | 8/1982 | Tschunt | |
| 4,384,359 A | 5/1983 | Franke | |
| 4,458,180 A | 7/1984 | Sohval et al. | |
| 4,570,106 A | 2/1986 | Sohval et al. | |
| 4,592,079 A | 5/1986 | Sohval et al. | |

(Continued)

FOREIGN PATENT DOCUMENTS

| | | |
|---|---|---|
| DE | 19513291 A1 | 10/1996 |
| DE | 102005044633 A1 | 2/2007 |

(Continued)

OTHER PUBLICATIONS

Search Report and Written Opinion from corresponding EP Application No. 11150872.7 dated May 13, 2011.

(Continued)

*Primary Examiner* — Hoon Song (57) ABSTRACT

A tube for generating x-rays includes a cathode adapted to emit electrons, a target positioned to receive the electrons from the cathode on a surface thereof, an anode adapted with an aperture and positioned between the cathode and the target and configured to accelerate the electrons toward the target, and a rotating system adapted to rotate the target about an axis, the rotating system located in a position facing the surface of the target.

23 Claims, 4 Drawing Sheets

(56) References Cited

U.S. PATENT DOCUMENTS

| | | | |
|---|---|---|---|
| 4,637,040 A | 1/1987 | Sohval et al. |
| 4,669,103 A | 5/1987 | Barnea |
| 4,672,651 A | 6/1987 | Horiba et al. |
| 4,866,745 A | 9/1989 | Akai |
| 4,894,775 A | 1/1990 | Kritchman et al. |
| 4,958,365 A | 9/1990 | Sohval et al. |
| 4,991,190 A | 2/1991 | Mori |
| 5,068,882 A | 11/1991 | Eberhard |
| 5,187,659 A | 2/1993 | Eberhard et al. |
| 5,228,069 A | 7/1993 | Arenson et al. |
| 5,375,156 A | 12/1994 | Kuo-Petravic |
| 5,490,193 A | 2/1996 | Kuroda et al. |
| 5,604,778 A | 2/1997 | Polacin et al. |
| 5,608,776 A | 3/1997 | Hsieh |
| 5,625,661 A | 4/1997 | Oikawa |
| 5,857,008 A | 1/1999 | Reinhold |
| 5,966,422 A | 10/1999 | Dafni et al. |
| 5,978,447 A * | 11/1999 | Carlson et al. ............... 378/132 |
| 6,198,790 B1 | 3/2001 | Pflaum |
| 6,208,706 B1 | 3/2001 | Campbell et al. |
| 6,229,870 B1 * | 5/2001 | Morgan ........................... 378/9 |
| 6,236,709 B1 | 5/2001 | Perry et al. |
| 6,272,199 B1 | 8/2001 | Sembritzki et al. |
| 6,385,288 B1 | 5/2002 | Kanematsu |
| 6,385,292 B1 | 5/2002 | Dunham et al. |
| 6,421,412 B1 | 7/2002 | Hsieh et al. |
| 6,553,096 B1 | 4/2003 | Zhou et al. |
| 6,654,440 B1 | 11/2003 | Hsieh |
| 6,731,716 B2 | 5/2004 | Mihara et al. |
| 6,760,407 B2 | 7/2004 | Price et al. |
| 6,807,248 B2 | 10/2004 | Mihara et al. |
| 6,816,573 B2 * | 11/2004 | Hirano et al. ................. 378/114 |
| 6,850,595 B2 | 2/2005 | Zhou et al. |
| 6,876,719 B2 | 4/2005 | Ozaki |
| 6,876,724 B2 | 4/2005 | Zhou et al. |
| 6,914,959 B2 * | 7/2005 | Bailey et al. .................... 378/65 |
| 6,937,689 B2 | 8/2005 | Zhao et al. |
| 6,947,522 B2 | 9/2005 | Wilson et al. |
| 6,975,703 B2 | 12/2005 | Wilson et al. |
| 6,980,623 B2 | 12/2005 | Dunham et al. |
| 6,980,627 B2 | 12/2005 | Qiu et al. |
| 6,983,035 B2 | 1/2006 | Price et al. |
| 7,003,077 B2 | 2/2006 | Jen et al. |
| 7,016,455 B2 | 3/2006 | Bruder et al. |
| 7,020,235 B2 | 3/2006 | Hornegger et al. |
| 7,039,153 B2 | 5/2006 | Bruder et al. |
| 7,042,975 B2 | 5/2006 | Heuscher |
| 7,062,006 B1 | 6/2006 | Pelc et al. |
| 7,065,179 B2 | 6/2006 | Block et al. |
| 7,068,749 B2 | 6/2006 | Kollegal et al. |
| 7,072,436 B2 | 7/2006 | Pelc |
| 7,082,182 B2 | 7/2006 | Zhou et al. |
| 7,085,343 B2 | 8/2006 | Shinno et al. |
| 7,085,351 B2 | 8/2006 | Lu et al. |
| 7,085,352 B2 | 8/2006 | Dunham |
| 7,103,138 B2 | 9/2006 | Pelc et al. |
| 7,120,222 B2 | 10/2006 | Hoffman |
| 7,127,025 B2 | 10/2006 | Bruder et al. |
| 7,130,369 B2 | 10/2006 | Bruder et al. |
| 7,145,981 B2 | 12/2006 | Pelc |
| 7,197,116 B2 | 3/2007 | Dunham et al. |
| 7,212,603 B2 | 5/2007 | Heismann et al. |
| 7,221,732 B1 | 5/2007 | Annis |
| 7,227,923 B2 | 6/2007 | Edic et al. |
| 7,227,924 B2 | 6/2007 | Zhou et al. |
| 7,245,692 B2 | 7/2007 | Lu et al. |
| 7,280,631 B2 | 10/2007 | De Man et al. |
| 7,281,850 B2 | 10/2007 | Varadharajan et al. |
| 7,302,030 B2 | 11/2007 | Bruder et al. |
| 7,305,063 B2 | 12/2007 | Heuscher |
| 7,333,587 B2 | 2/2008 | De Man et al. |
| 7,336,761 B2 | 2/2008 | Udpa et al. |
| 2003/0076972 A1 | 4/2003 | Maejima |
| 2004/0120449 A1 | 6/2004 | Edic et al. |
| 2004/0146143 A1 | 7/2004 | Price et al. |
| 2004/0213378 A1 | 10/2004 | Zhou et al. |
| 2004/0240616 A1 | 12/2004 | Qiu et al. |
| 2004/0247082 A1 | 12/2004 | Hoffman |
| 2004/0258196 A1 | 12/2004 | Lounsberry |
| 2005/0031069 A1 | 2/2005 | Kaucic et al. |
| 2005/0041771 A1 | 2/2005 | Kuo-Petravic et al. |
| 2005/0100125 A1 | 5/2005 | Heismann |
| 2005/0135550 A1 | 6/2005 | Man et al. |
| 2005/0161609 A1 | 7/2005 | Heismann et al. |
| 2005/0175151 A1 | 8/2005 | Dunham et al. |
| 2005/0226363 A1 | 10/2005 | Edic et al. |
| 2005/0226364 A1 | 10/2005 | Bernard et al. |
| 2005/0226385 A1 | 10/2005 | Simpson et al. |
| 2005/0232389 A1 | 10/2005 | Klingenbeck-Regn |
| 2005/0238136 A1 | 10/2005 | Bruder et al. |
| 2005/0265520 A1 | 12/2005 | Huber et al. |
| 2005/0281379 A1 | 12/2005 | Qiu et al. |
| 2006/0018423 A1 | 1/2006 | Bruder et al. |
| 2006/0018432 A1 | 1/2006 | Zhou et al. |
| 2006/0023832 A1 | 2/2006 | Edic et al. |
| 2006/0023833 A1 * | 2/2006 | Seufert ............................ 378/9 |
| 2006/0045235 A1 | 3/2006 | Bruder et al. |
| 2006/0098780 A1 | 5/2006 | Dunham et al. |
| 2006/0146984 A1 | 7/2006 | Bruder et al. |
| 2006/0159221 A1 | 7/2006 | Popescu |
| 2006/0165213 A1 | 7/2006 | Hambuchen et al. |
| 2006/0210014 A1 | 9/2006 | Okumura et al. |
| 2006/0210015 A1 | 9/2006 | Pelc et al. |
| 2006/0233297 A1 | 10/2006 | Ishiyama |
| 2006/0245537 A1 | 11/2006 | Bakai et al. |
| 2006/0285633 A1 | 12/2006 | Sukovic et al. |
| 2007/0009081 A1 | 1/2007 | Zhou et al. |
| 2007/0009088 A1 | 1/2007 | Edic et al. |
| 2007/0025498 A1 | 2/2007 | Matsuda |
| 2007/0025499 A1 | 2/2007 | Bruder et al. |
| 2007/0053489 A1 | 3/2007 | Lu et al. |
| 2007/0081622 A1 | 4/2007 | Bruder et al. |
| 2007/0086564 A1 | 4/2007 | Bruder et al. |
| 2007/0098136 A1 | 5/2007 | Lutz |
| 2008/0095317 A1 * | 4/2008 | Lemaitre ...................... 378/138 |
| 2008/0123803 A1 | 5/2008 | De Man et al. |
| 2009/0279667 A1 | 11/2009 | Rogers et al. |
| 2011/0142193 A1 * | 6/2011 | Frontera et al. ................. 378/16 |

FOREIGN PATENT DOCUMENTS

| | | |
|---|---|---|
| EP | 1277439 A1 | 1/2003 |
| EP | 1016376 B1 | 12/2006 |
| EP | 1772100 A1 | 4/2007 |
| JP | 491589 Y1 | 1/1974 |
| JP | 5619855 A | 2/1981 |
| JP | 08315758 A | 11/1996 |
| JP | 2001273860 A | 10/2001 |
| WO | 9907283 A1 | 2/1999 |
| WO | 0160258 A1 | 8/2001 |
| WO | 0226134 A1 | 4/2002 |
| WO | 03063195 A1 | 7/2003 |
| WO | 2005016113 A2 | 2/2005 |
| WO | 2007135614 A1 | 11/2007 |
| WO | 2008021661 A3 | 2/2008 |
| WO | 2008024586 A2 | 2/2008 |
| WO | 2008053403 A2 | 5/2008 |
| WO | 2008053403 A3 | 5/2008 |
| WO | 2009136349 A2 | 11/2009 |

OTHER PUBLICATIONS

Unofficial English translation of Japanese Office Action issued in connection with corresponding JP Application No. 2011-007396 on Aug. 12, 2014.

Unofficial English Translation of Japanese Office Action issued in connection with corresponding JP Application No. 2011007396 on Feb. 17, 2015.

* cited by examiner

APPARATUS FOR WIDE COVERAGE COMPUTED TOMOGRAPHY AND METHOD OF CONSTRUCTING SAME

BACKGROUND OF THE INVENTION

Embodiments of the invention relate generally to x-ray tubes and, more particularly, to an apparatus for wide coverage computed tomography and a method of constructing same.

Computed tomography X-ray imaging systems typically include an x-ray tube, a detector, and a gantry assembly to support the x-ray tube and the detector. In operation, an imaging table, on which an object is positioned, is located between the x-ray tube and the detector. The x-ray tube typically emits radiation, such as x-rays, toward the object. The radiation typically passes through the object on the imaging table and impinges on the detector. As radiation passes through the object, internal structures of the object cause spatial variances in the radiation received at the detector. The detector converts the received radiation to electrical signals and then transmits data received, and the system translates the radiation variances into an image, which may be used to evaluate the internal structure of the object. One skilled in the art will recognize that the object may include, but is not limited to, a patient in a medical imaging procedure and an inanimate object as in, for instance, a package in an x-ray scanner or computed tomography (CT) package scanner.

A typical x-ray tube includes a cathode that provides a focused high energy electron beam that is accelerated across a cathode-to-anode vacuum gap and produces x-rays upon impact with an active material or target provided. Because of the high temperatures generated when the electron beam strikes the target, typically the target assembly is rotated at high rotational speed for purposes of cooling the target.

As such, the x-ray tube also includes a rotating system that rotates the target for the purpose of distributing the heat generated at a focal spot on the target. The rotating subsystem is typically rotated by an induction motor having a cylindrical rotor built into an axle that supports a disc-shaped target and an iron stator structure with copper windings that surrounds an elongated neck of the x-ray tube. The rotor of the rotating subsystem assembly is driven by the stator.

Computed tomography systems are continuing to increase the size of the detector along a patient body or Z-axis, so that entire organs (e.g., heart, brain) can be imaged in one rotation of the gantry. Consequently, a vertical opening angle of the x-ray transmissive window in the x-ray tube is typically broadened further to allow for irradiation of the examination object covering a wider extent along the Z-axis. As z-axis coverage increases, a fan out of the x-ray beam along the wider z-axis can cause image artifacts or so-call cone-beam artifact due to missing data in the image reconstruction. Additionally, a target angle of the x-ray tube is typically increased to accommodate the larger vertical opening angle and fully cover the detector. This larger target angle significantly reduces an amount of x-ray flux that can be generated due to temperature limitations on the rotating target (holding the optical focal spot size constant as determined by the well-known line focus principle).

A theoretical solution to these problems is to provide two or more focal spots spaced apart from each other along the z-axis and operating in an on/off sequential manner. This optical configuration can allow for an overlap of x-ray beams from each of the focal spots over some extent of the center of view and achieve a reduction in the cone-beam angle, thereby, greatly decreasing cone-beam artifacts. This configuration also allows for a reduction in the target angles and consequently higher x-ray output. One possible solution to the problem is to make an x-ray tube with two targets instead of only one target such that the two focal points are offset along the z-axis or axial dimension. The difficulty with that solution is, however, that the use of two axially offset targets may require an inordinately large and complicated x-ray tube. That is, such a tube may have two targets in one vacuum cavity, two cathodes and two high voltage insulators, one on each end to feed the cathode. Such a tube would be very costly and have reliability implications, that is, if one of the cathodes or targets were to fail, the entire tube would need to be replaced to maintain full functionality, resulting in a costly replacement.

Another solution to the problem would be to abut or configure end to end two conventional x-ray tubes, however, typical CT x-ray tubes are simply physically too lengthy to make that solution practical. With the present x-ray tubes, the tubes include a cathode, insulator and other systems for focusing the high energy electrons onto the target, and that apparatus is located facing the target face of the rotating anode. At the same time, the rotating system for rotating the anode is also cumbersome and that system is located facing the opposite side, or non-target side surface of the anode. Together, two conventional x-ray sources placed end-to-end along their respective rotational axes would space the focal spots too far from each other to make a useable source for the desired system configuration. For example, a desired axial spacing on the z-axis in a two focal spot system is 120 mm coverage at the system iso-center or typically in the range of 60-120 mm. Therefore, the advantages derived from the presence of two focal points is not feasible with conventional x-ray tubes.

Accordingly, it would be advantageous to have an x-ray tube that could be abutted together with another x-ray tube and achieve a spaced apart distance for the focal points that is within the desired range and thereby gain the advantage of using a combined apparatus with two x-ray tubes and two focal points.

BRIEF DESCRIPTION OF THE INVENTION

Embodiments of the invention provide an apparatus and method of constructing an apparatus that allows the abutting together of two x-ray tubes while achieving a distance between the focal points of the individual tubes within the desired range of distances.

According to one aspect of the invention, a tube for generating x-rays includes a cathode adapted to emit electrons, a target positioned to receive the electrons from the cathode on a surface thereof, an anode with an aperture and positioned between the cathode and the target and configured to accelerate the electrons toward the target, and a rotating system adapted to rotate the target about an axis, the rotating system located in a position facing the surface of the target.

In accordance with another aspect of the invention, an apparatus for producing two beams of x-ray radiation includes a first x-ray tube that includes a first cathode adapted to emit a first beam of electrons toward a first anode, a first target having a first surface to receive the first beam of electrons emitted by the first cathode to generate a first beam of x-rays, a first rotating system adapted to rotate the first target about a first axis, the first rotating system located in a position facing the first surface. The apparatus includes a second x-ray tube that includes a second cathode adapted to emit a second beam of electrons toward a second anode, a second target having a second surface to receive the second beam of electrons emitted by the second cathode to generate a second beam of x-rays, a second rotating system adapted to rotate the second target about a second axis, the second rotating system located in a position facing the second surface, wherein the first and second x-ray tubes are in close proximity to each other and configured to emit the first and second beams of x-rays toward an object to be imaged.

Yet another aspect of the invention includes a method of fabricating an x-ray tube includes providing a casing, providing a cathode adapted to generate electrons, providing a target having a surface adapted to emit x-ray radiation upon receiving electrons emitted by the cathode, positioning an anode between the cathode and the target, the anode configured to accelerate the electrons toward the target, providing a rotating system adapted to rotate the target about an axis, placing the target within the casing, placing the cathode within the casing in a location facing the surface of the target to direct and electron beam toward a focal point on the target, and placing the rotating system within the casing in a location facing the surface of the target.

Still another aspect of the invention includes a method of constructing a combined apparatus providing first and second streams of x-ray radiation including providing a first target in a first x-ray tube that is rotational about a first rotational axis, the first target having a first focal spot on a first face thereof to generate the first stream of x-ray radiation, providing a second target in a second x-ray tube that is rotational about a second rotational axis, the second target having a second focal spot on a second face thereof to generate the second stream of x-ray radiation, and placing the first x-ray tube in an abutting position proximate to the second x-ray tube such that the first face of the first target faces away from the second x-ray tube, and such that the second face of the second target faces away from the first x-ray tube.

Various other features and advantages of the invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION

Figure 1:
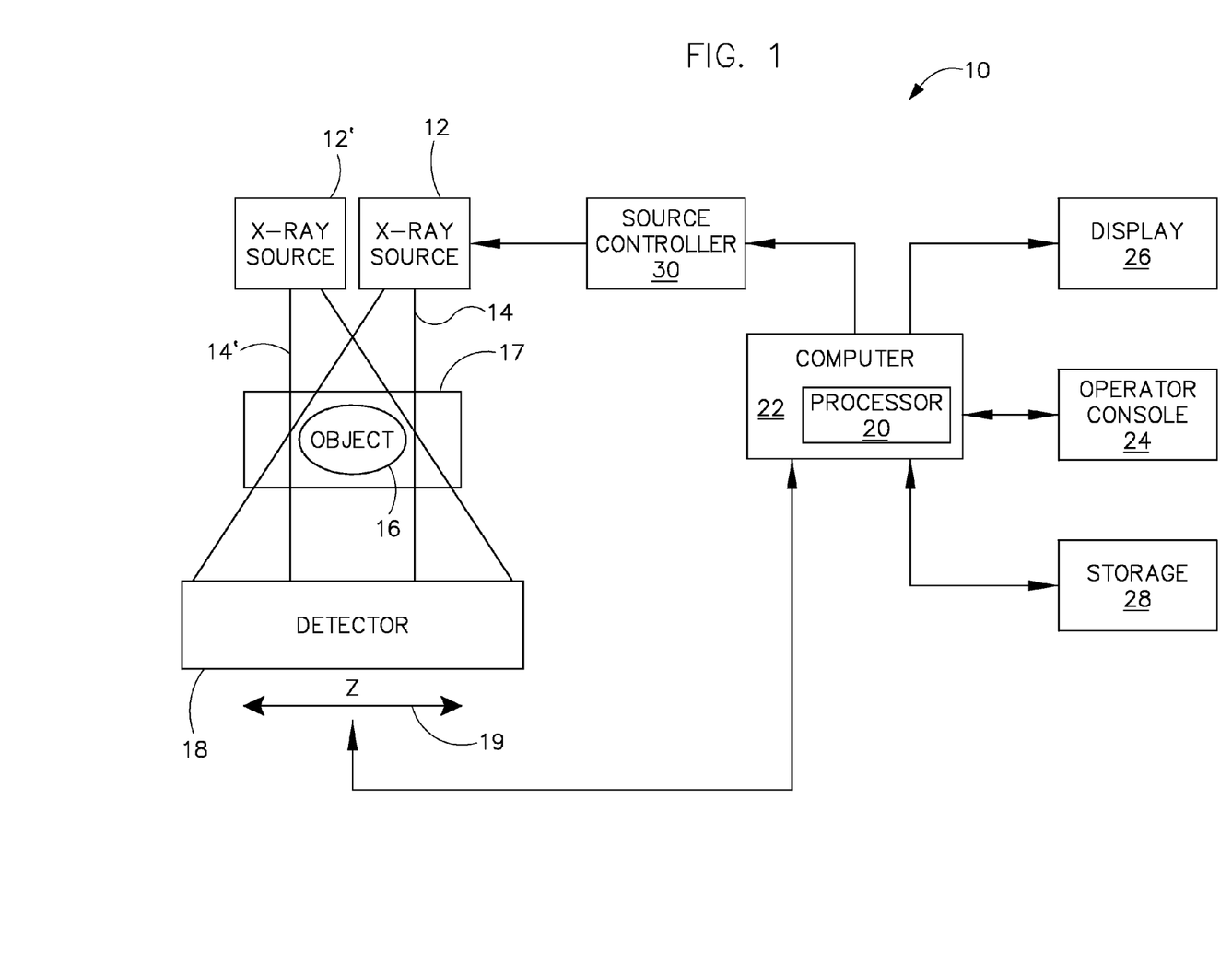
FIG. 1 is a block diagram of an imaging system that can benefit from incorporation of an embodiment of the invention.

FIG. 1 is a block diagram of an embodiment of an imaging system 10 designed both to acquire original image data and to process the image data for display and/or analysis in accordance with the invention. It will be appreciated by those skilled in the art that the invention is applicable to numerous medical imaging systems implementing an x-ray tube, such as a CT system, an x-ray system, a vascular system, and a mammography system. Other imaging systems such as computed tomography systems and digital radiography systems, which acquire image three dimensional data for a volume, also benefit from the invention. The following discussion of x-ray system 10 is merely an example of one such implementation and is not intended to be limiting in terms of modality.

As shown in FIG. 1, x-ray system 10 represents elements of a computed tomography (CT) system that includes x-ray sources 12 and 12' configured to project respective beams of x-rays 14 and 14' through an organ such as a heart or an item within a piece of luggage 16 within an object or patient 17. Object 17 may include a human subject, pieces of baggage, or other objects desired to be scanned. X-ray sources 12, 12' may be conventional x-ray tubes producing x-rays having a spectrum of energies that range, typically, from 30 keV to 200 keV. The x-rays 14, 14' pass through organ 16 and object 17 and, after being attenuated, impinge upon a detector assembly 18 extending along a patient or z-axis 19. For a computed tomography system, the x-ray beams 14 and 14' are gridded on and off in alternating succession such that the detector is receiving x-rays from only one source during a reconstructed view time. Each detector module in detector assembly 18 produces an analog electrical signal that represents the intensity of an impinging x-ray beam, and hence the attenuated beam, as it passes through the organ 16. In one embodiment, detector assembly 18 is a scintillation based detector assembly, however, it is also envisioned that direct-conversion type detectors (e.g., CZT detectors, etc.) may also be implemented.

A processor 20 receives the signals from the detector 18 and generates an image corresponding to the organ 16 or object 17 being scanned. A computer 22 communicates with processor 20 to enable an operator, using operator console 24, to control the scanning parameters and to view the generated image. That is, operator console 24 includes some form of operator interface, such as a keyboard, mouse, voice activated controller, or any other suitable input apparatus that allows an operator to control the x-ray system 10 and view the reconstructed image or other data from computer 22 on a display unit 26. Additionally, console 24 allows an operator to store the generated image in a storage device 28 which may include hard drives, floppy discs, compact discs, etc. The operator may also use console 24 to provide commands and instructions to computer 22 for controlling a source controller 30 that provides power and timing signals to x-ray source 12.

As illustrated, each x-ray source 12, 12' provides x-rays that pass through object 17, and in combination, x-rays pass from each source 12, 12' to detector assembly 18. As such, embodiments of the invention provide sufficient coverage along z-axis 19 for complete organ coverage, to include, as examples, a heart or a brain. As such, x-ray sources 12, 12' may be rotated in conjunction with detector assembly 18 about object 17 with sufficient speed such that an entire organ, such as a heart, may be imaged in a single rotation and without cone-beam or other artifacts related to limited z-axis coverage. Further, system 10 includes a cost improvement over other systems by providing separate and replaceable sources 12, 12'. In such fashion, in the event that a source fails or otherwise needs replacement, only one of the sources 12, 12' need be replaced, thus simplifying replacement and reducing overall system cost of operation and maintenance. Further, in the event that one of the sources 12, 12' fails, system 10 may be caused to operate using the remaining source 12 or 12' that has not experienced failure. Thus, system 10 may operate and provide useful information, albeit from only one of the sources 12, 12', after one of the sources 12, 12' has failed, enabling useful data to be obtained despite a source failure. System 10 in fact enables multiple modes of operation that may use one source or both sources 12, 12', according to embodiments of the invention.

Figure 2:
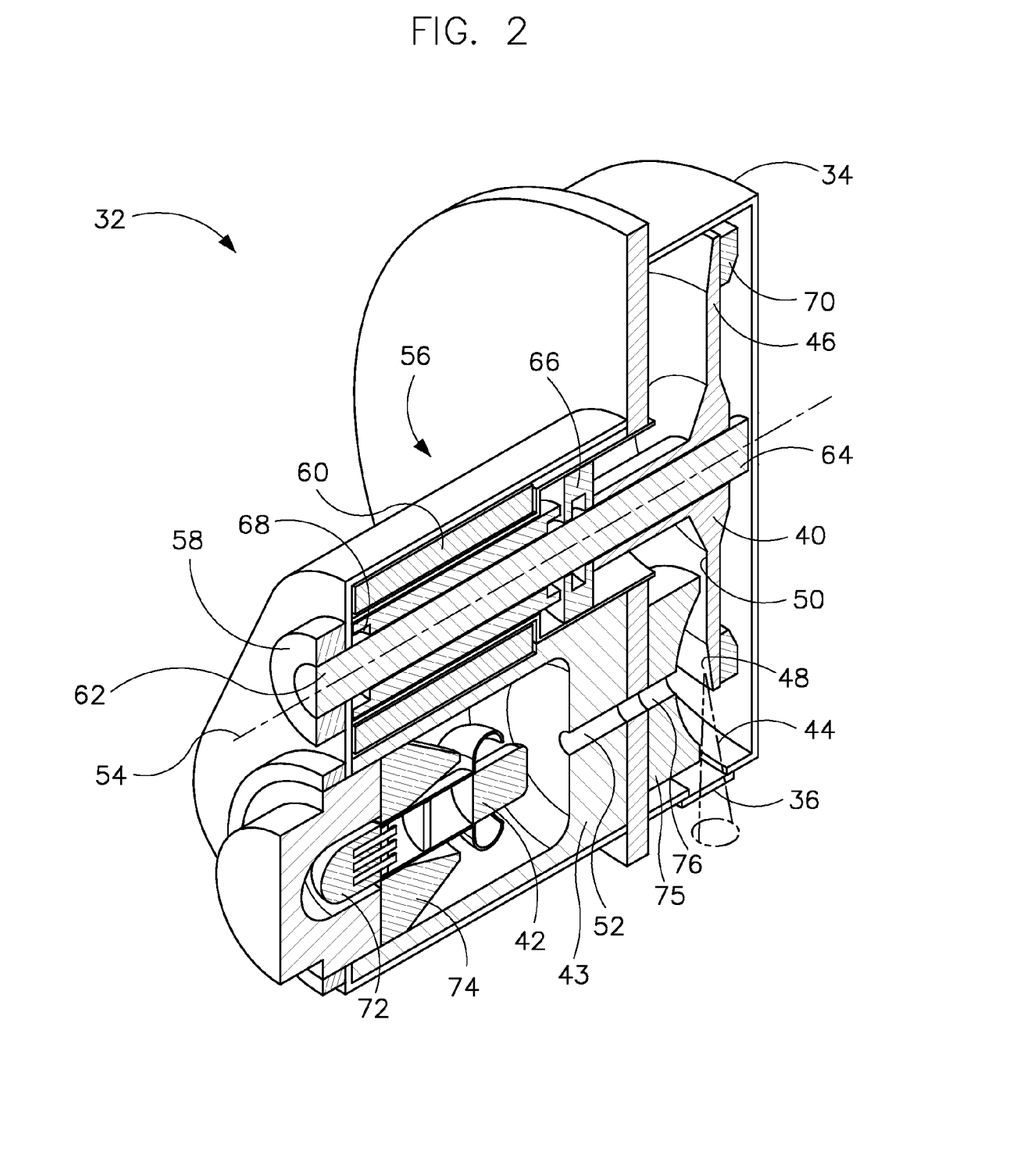
FIG. 2 is a cutaway perspective view of the x-ray tube constructed in accordance with the invention.

FIG. 2 illustrates a perspective cutaway view of an x-ray source or tube 32 constructed in accordance with the invention. As can be seen, the x-ray tube 32 includes a casing 34 having a radiation emission passage 36 formed therein. The casing 34 encloses a vacuum and houses a target 40 and a cathode 42. An anode 43 provided with an aperture 52 for conveyance of electrons is positioned between cathode 42 and target 40. X-rays 44 are produced when high-speed electrons are suddenly decelerated when directed from the cathode 42 to the target 40 via a potential difference applied between cathode 42 and anode 43 of, for example, 60 thousand volts or more in the case of CT applications.

The electrons impact a material layer or target material 46 at a focal point 48 and x-rays 44 emit therefrom. The point of impact is typically referred to in the industry as the focal spot, which forms a circular region or track on a surface of target material 46, and is visually evident on the target surface after operation of the x-ray tube 32. As can be seen, target material 46 is provided on one surface 50 of target 40 and cathode 42 is located at a position on the same side of that surface 50 so that the high-energy electrons can pass from cathode 42 through an aperture 52 of anode 43 to impinge upon target 46 at focal point 48. The x-rays 44 emit through radiation emission passage 36 toward a detector array, such as detector 18 of FIG. 1. The angular configuration of the target at the focal spot results in the emission of radiation toward the radial passage 36, which angle is 7 degrees to 12 degrees relative to a perpendicular orientation of the target 46 to an axis of rotation 54. To avoid overheating target 40 from the electrons, target 40 is rotated at a high rate of speed about the rotational axis or centerline 54 at, for example, 90-250 Hz.

A rotating system 56 is provided to rotate target 40 and includes a center shaft 58, that can be a solid or hollow shaft, attached to a rotor 60 at a first end 62 and attached to the target 40 at a second end 64. A pair of bearings 66, 68 are used about center shaft 58 to allow center shaft 58 to rotate freely within casing 34. A stator (not shown) is positioned radially external to rotor 60 and drives center shaft 58, which rotationally drives target 40. Alternately an embodiment includes a rotating subsystem (not shown) in which the center shaft is stationary and an outer cylinder supporting the target material 46 and attached to the rotor 60 rotates about the stationary shaft around a central axis of the stationary shaft. As shown in FIG. 2, a heat storage medium 70, such as graphite, may be used to sink and/or dissipate heat built-up near target material 46. Further components of the x-ray tube 32 include a cable connector 72 and a high voltage insulator 74 as well as an electron collector 75 that has an aperture 76 for electrons to stream from cathode 42 to focal point 48 of target 40.

As can be seen, rotating system 56 is located within casing 34 on the same side of the surface 50 of the target 40 as the cathode 42. That is, both the cathode 42 and the rotating system 56 are generally aligned and face the same surface 50 of the target 40 that also includes the target 46 and the focal point 48, thus the overall length of the x-ray tube is greatly reduced and is relatively compact. A longitudinal axis of the cathode is basically parallel to the centerline 54 of the center shaft 58 and axis of rotation of the target 40. In embodiments described, high voltage is applied to electrons emitted from cathode 42 to target 40 via anode 43. In one embodiment, anode 43 is grounded and a high voltage, such as 60 keV or greater, is applied to cathode 42. However, the invention is not to be so limited and in another embodiment target 40 serves as the anode and is, likewise, grounded. In still another embodiment a negative voltage is applied to cathode 42 and a positive voltage is applied to anode 43 and/or target 40.

Figure 3:
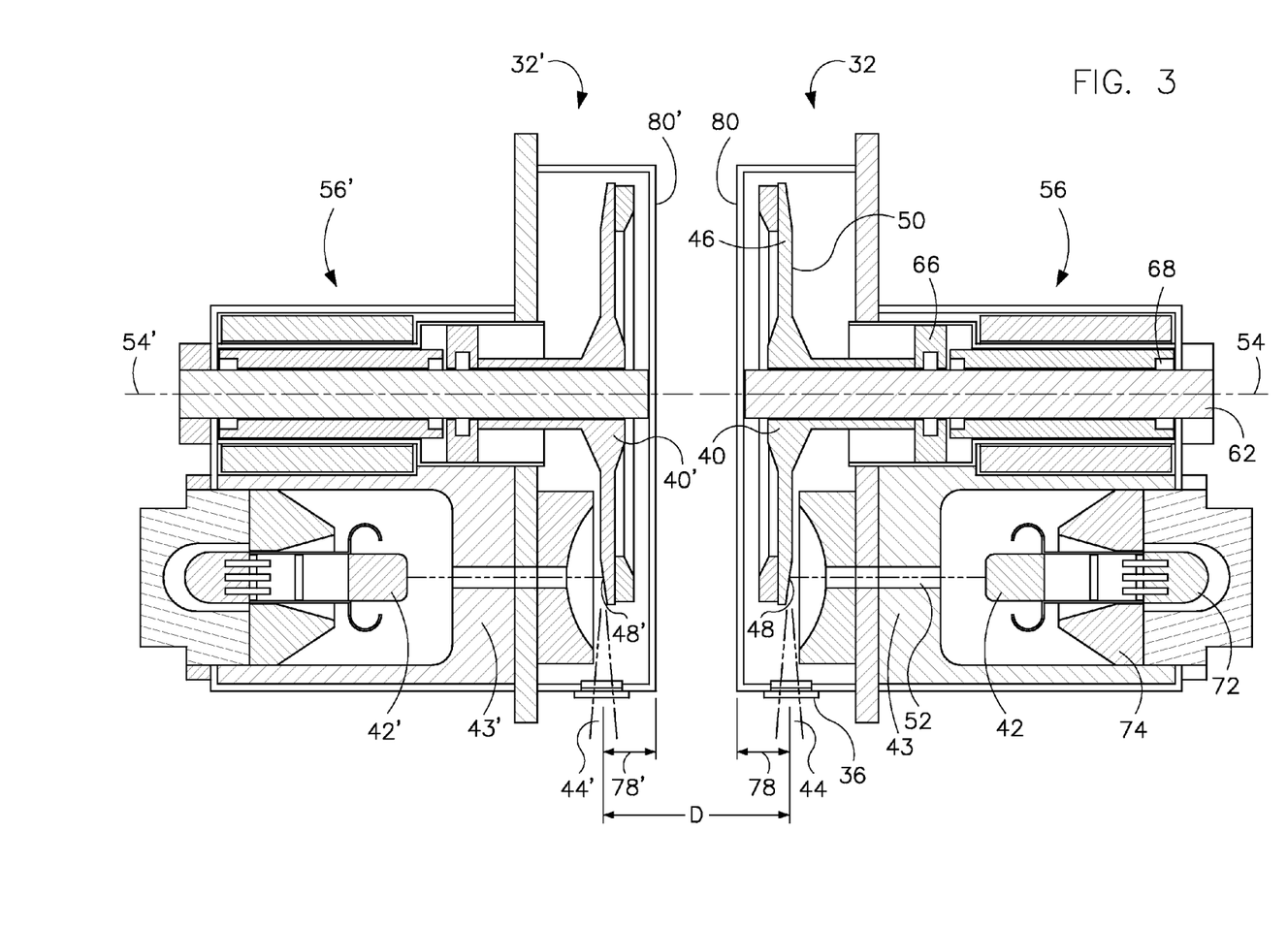
FIG. 3 is a cutaway side view of a two x-ray tube apparatus of the invention.

Turning now to FIG. 3, taken along with FIG. 2, there is shown a side view, cut away, illustrating an apparatus made up of a combination of two of the x-ray tubes, 32 and 32', that are both constructed in accordance with the single x-ray tube 32 shown and described with respect to FIG. 2. X-ray tubes 32 and 32' are abutted against each other, according to an embodiment of the invention.

Accordingly, each of the x-ray tubes 32, 32' has a focal point 48, 48' and the respective focal points 48, 48' are in close proximity to each other due to the unique construction of the x-ray tubes 32, 32'. In the exemplary embodiment, a distance D between the focal points 48, 48' are within a range of about 60-120 mm. Thus, by the particular location of the cathodes 42, 42' as well as the rotating systems 56, 56', an overall axial length of the x-ray tubes 32, 32' is shortened, and more particularly an axial distance 78, 78' between focal points 48, 48' and a respective end 80, 80', to the point that distance D between the focal points 48, 48' are within the desired range. As such, x-ray tubes 32 and 32' may be aligned axially to each other, along for instance their respective rotational axes 54, 54', such that their focal spots 48, 48' can be aligned within a system, such as system 10 of FIG. 1. An optimal distance D between focal spots depends on several CT system variables including but not limited to an imaging field of view at system isocenter, and a relative distance between the x-ray sources 32, 32', patient 17 and detector 18.

With the FIG. 3 embodiment, the control system 30, illustrated in FIG. 1 can be used to alternate the firing of the cathodes 42, 42' producing x-ray beams upon firing. That is, each cathode 42, 42' can be fired individually so as to alternate between the firing of the cathode 42 and the firing of the cathode 42'. In addition, with the FIG. 3 embodiment, the control system of FIG. 1 can also be used to provide a dual energy system, such that one of the x-ray tubes is operated with a different energy than the other x-ray tube. As such, in a dual energy or multiple energy scanning, one cathode can be operated at for example 80 keV while the other cathode can be operated at for example 140 keV. As such, dual or multi-energy x-rays may be generated in an imaging system, such as imaging system 10 of FIG. 1, which may be used to form multi-energy images in a base material decomposition, as an example. Further, in the dual source system illustrated in FIG. 3 having cathodes 42, 42' that can be alternately fired, a performance benefit may be realized in that life of components such as the target may be increased, due to the approximate 50% duty cycle experienced in such operation. Therefore, a peak power and consequently a magnitude of an x-ray flux emitting from the respective target may likewise be increased, versus a system employing one source. Additionally, a target angle for the illustrated two source system can be significantly smaller when compared to a system employing one source, as understood in the art. Therefore, the two source system illustrated in FIG. 3 can produce a much higher x-ray flux than a single source system with this larger Z-axis coverage.

Figure 4:
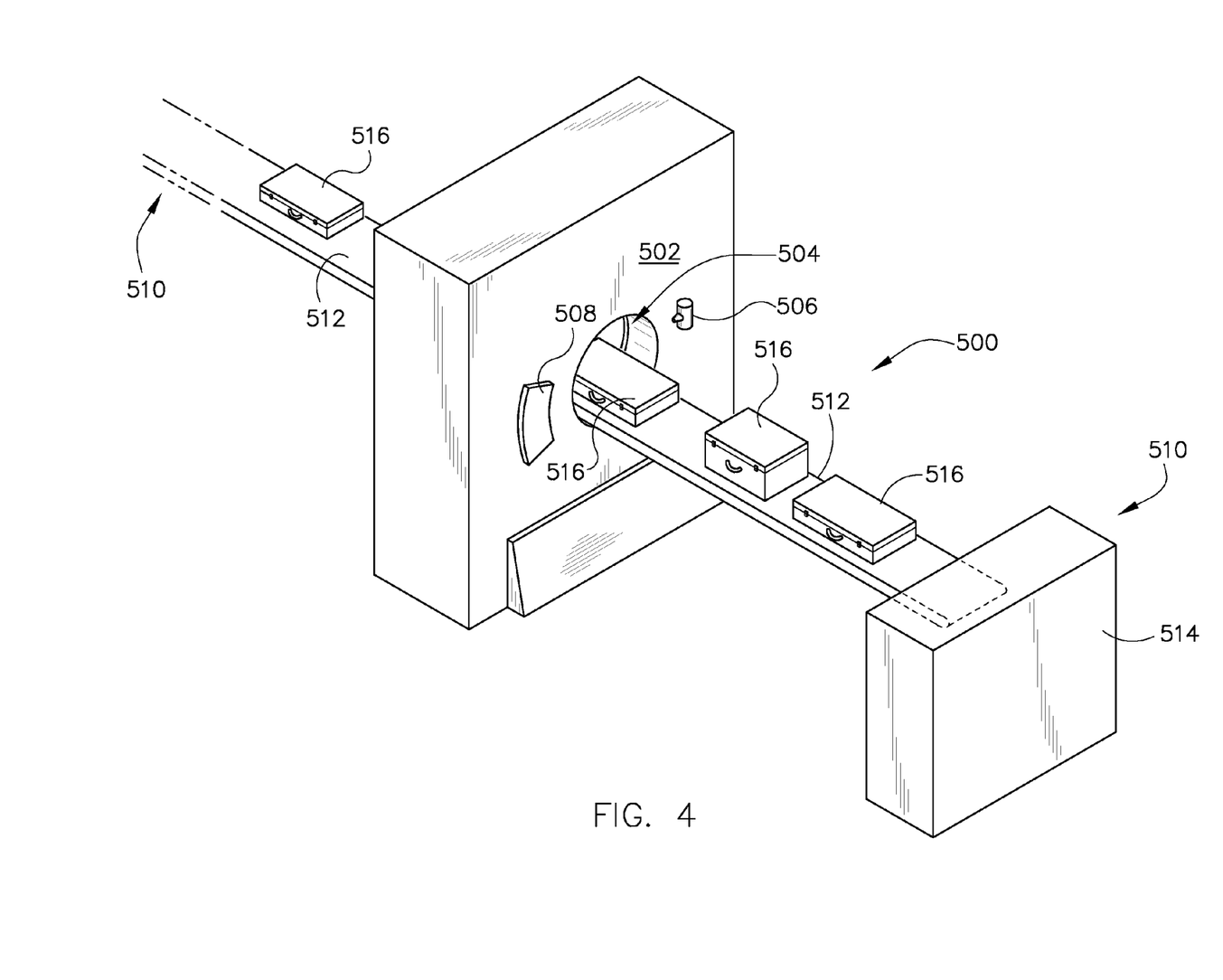
FIG. 4 is a pictorial view of a CT system for use with a non-invasive package inspection system.

Referring now to FIG. 4, there is shown a package/baggage inspection system 500 that can use the x-ray tube or tubes of the invention and which includes a rotatable gantry 502 having an opening 504 therein through which packages or pieces of baggage may pass. The rotatable gantry 502 houses one or more x-ray energy sources 506 as well as a detector assembly 508 having scintillator arrays comprised of scintillator cells. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc.

According to an embodiment of the invention, a tube for generating x-rays includes a cathode adapted to emit electrons, a target positioned to receive the electrons from the cathode on a surface thereof, an anode adapted with an aperture and positioned between the cathode and the target and configured to accelerate the electrons toward the target, and a rotating system adapted to rotate the target about an axis, the rotating system located in a position facing the surface of the target.

According to another embodiment of the invention, an apparatus for producing two beams of x-ray radiation includes a first x-ray tube that includes a first cathode adapted to emit a first beam of electrons toward a first anode, a first target having a first surface to receive the first beam of electrons emitted by the first cathode to generate a first beam of x-rays, a first rotating system adapted to rotate the first target about a first axis, the first rotating system located in a position facing the first surface. The apparatus includes a second x-ray tube that includes a second cathode adapted to emit a second beam of electrons toward a second anode, a second target having a second surface to receive the second beam of electrons emitted by the second cathode to generate a second beam of x-rays, a second rotating system adapted to rotate the second target about a second axis, the second rotating system located in a position facing the second surface, wherein the first and second x-ray tubes are in close proximity to each other and configured to emit the first and second beams of x-rays toward an object to be imaged.

Yet another embodiment of the invention includes a method of fabricating an x-ray tube includes providing a casing, providing a cathode adapted to generate electrons, providing a target having a surface adapted to emit x-ray radiation upon receiving electrons emitted by the cathode, positioning an anode between the cathode and the target, the anode configured to accelerate the electrons toward the target, providing a rotating system adapted to rotate the target about an axis, placing the target within the casing, placing the cathode within the casing in a location facing the surface of the target to direct and electron beam toward a focal point on the target, and placing the rotating system within the casing in a location facing the surface of the target.

Still another embodiment of the invention includes a method of constructing a combined apparatus providing first and second streams of x-ray radiation including providing a first target in a first x-ray tube that is rotational about a first rotational axis, the first target having a first focal spot on a first face thereof to generate the first stream of x-ray radiation, providing a second target in a second x-ray tube that is rotational about a second rotational axis, the second target having a second focal spot on a second face thereof to generate the second stream of x-ray radiation, and placing the first x-ray tube in an abutting position proximate to the second x-ray tube such that the first face of the first target faces away from the second x-ray tube, and such that the second face of the second target faces away from the first x-ray tube.

The invention has been described in terms of the preferred embodiment, and it is recognized that equivalents, alternatives, and modifications, aside from those expressly stated, are possible and within the scope of the appending claims.

What is claimed is:

1. A tube for generating x-rays comprising:
    a cathode adapted to emit electrons;
    a target positioned to receive the electrons from the cathode on a surface thereof;
    an anode adapted with an aperture and positioned between the cathode and the target and configured to accelerate the electrons toward the surface of the target, wherein the anode is grounded;
    a rotating system adapted to rotate the target about an axis, the rotating system attached to the target and located in a position facing the surface of the target that is positioned to receive the electrons from the cathode;
    a high voltage insulator positioned between the cathode and the rotating system to electrically insulate the rotating system from the cathode; and
    an electron collector having a first aperture therein and positioned between the anode and the target;
    wherein the anode and the electron collector are positioned such that the electrons pass through the first aperture of the electron collector and through the aperture of the anode.

2. The tube of claim 1 wherein the rotating system includes a rotor, a bearing system and a shaft connected between the rotor and the target to rotate the target.

3. The tube of claim 2 wherein a longitudinal axis of the shaft is parallel to a longitudinal axis of the cathode.

4. The tube of claim 1 wherein the anode comprises the aperture positioned to pass the electrons therethrough.

5. The tube of claim 1 wherein the tube is incorporated into a baggage inspection system.

6. An apparatus for producing two beams of x-ray radiation comprising:
    a first x-ray tube enclosure that encloses a first volume, the first x-ray tube comprising:
        a first cathode adapted to emit a first beam of electrons toward a first anode;
        a first target having a first surface to receive the first beam of electrons emitted by the first cathode to generate a first beam of x-rays; and
        a first rotating system adapted to rotate the first target about a first axis, the first rotating system located in a position facing the first surface; and
    a second x-ray tube enclosure that encloses a second volume that is separate from the first enclosure, the second x-ray tube comprising:
        a second cathode adapted to emit a second beam of electrons toward a second anode;
        a second target having a second surface to receive the second beam of electrons emitted by the second cathode to generate a second beam of x-rays; and
        a second rotating system adapted to rotate the second target about a second axis, the second rotating system located in a position facing the second surface;
    wherein the first and second x-ray tubes are in close proximity to each other and aligned with one another along the first and second axes, and configured to emit the first and second beams of x-rays toward an object to be imaged, and wherein a path of the first beam of electrons and a path of the second beam of electrons are directed in directions along axes that are opposite to one another.

7. The apparatus of claim 6 wherein the first anode is positioned between the first cathode and the first target, the first anode configured to accelerate the first beam of electrons via a first voltage applied between the first cathode and the first anode; and wherein the second anode is positioned between the second cathode and the second target, the second anode configured to accelerate the second beam of electrons via a second voltage applied between the second cathode and the second anode.

8. The apparatus of claim 6 wherein the path of the first beam of electrons and a path of the second beam of electrons are directed along the same axis.

9. The apparatus of claim 6 wherein the first cathode directs the first beam of electrons toward a first focal point on the first surface of the first target and the second cathode directs the second beam of electrons toward a second focal point on the second surface of the second target.

10. The apparatus of claim 6 wherein the apparatus includes a control system adapted to separately activate the first and second cathodes.

11. The apparatus of claim 10 wherein the control system activates the first and second cathodes on an alternating basis.

12. The apparatus of claim 6 wherein the apparatus includes a control system to energize the first and second cathodes at different energy levels.

13. A method of constructing a combined apparatus providing first and second streams of x-ray radiation comprising:
providing a first target in a first x-ray tube enclosure that is rotational about a first rotational axis, the first target having a first focal spot on a first face thereof to generate the first stream of x-ray radiation;
providing a second target in a second x-ray tube enclosure that is rotational about a second rotational axis, the second target having a second focal spot on a second face thereof to generate the second stream of x-ray radiation, the second x-ray tube enclosure enclosing a volume that is separate from the first x-ray tube enclosure; and
placing the first x-ray tube in an abutting position proximate to the second x-ray tube such that the first face of the first target faces away from the second x-ray tube, and such that the second face of the second target faces away from the first x-ray tube, and such that first and second x-ray tubes are aligned with one another along the first and second rotational axes and such that the first and second x-ray tubes are aligned axially to each other along their respective first and second rotational axes.

14. The method of claim 13 comprising positioning the first rotational axis substantially colinear with the second rotational axis.

15. The method of claim 13 wherein the step of placing the first x-ray tube in the abutting position proximate to the second x-ray tube comprises placing the first and second x-ray tubes such that the distance between the first and second focal spots is between approximately 60 and 120 mm.

16. The method of claim 13 comprising:
fabricating the first x-ray tube by the steps of:
providing a first casing to form the first x-ray tube enclosure;
providing a first cathode adapted to emit a first stream of high energy electrons toward the first focal spot;
providing the first target having the first face adapted to emit the first stream of x-ray radiation from the first focal spot upon receiving the first stream of high energy electrons emitted by the first cathode;
providing a first rotating system adapted to rotate the first target about the first rotational axis;
placing a first anode within the first x-ray tube enclosure and between the first cathode and the first target;
placing the first cathode within the first x-ray tube enclosure and in a location facing the first face of the first target to direct the first stream of high energy electrons toward the first focal point on the first target; and
placing the first rotating system within the first x-ray tube enclosure and in a location facing the first face of the first target;
fabricating the second x-ray tube by the steps of:
providing a second casing to form the second x-ray tube enclosure;
providing a second cathode adapted to emit a second stream of high energy electrons toward the second focal point;
providing the second target having a second face adapted to emit the second stream of x-ray radiation upon receiving the second stream of high energy electrons emitted by the second cathode;
providing a second rotating system adapted to rotate the second target about the second rotational axis;
placing a second anode within the second x-ray tube enclosure and between the second cathode and the second target;
placing the second cathode within the second x-ray tube enclosure and in a location facing the second face of the second target to direct the second stream of high energy electrons toward the second focal point on the second target; and
placing the second rotating system within the second x-ray tube enclosure and in a location facing the second face of the second target.

17. The apparatus of claim 6 wherein the first target and the second target are configured to be operated separately from one another.

18. The apparatus of claim 9 wherein the first and second focal points are positioned such that they emit toward a detector from positions that are axially separated from one another, along an axis that is parallel to a rotational axis of one of the first and second rotating systems.

19. The apparatus of claim 18 wherein the first and second focal points are positioned axially apart a distance of about 60-120 mm.

20. The apparatus of claim 9 wherein first and second x-ray tubes are positioned such that the first cathode emits the first beam of electrons toward the first focal point in a first direction, and the second cathode emits the second beam of electrons toward the second focal point in a second direction that is opposite the first direction.

21. The apparatus of claim 19 wherein the first direction and the second direction are toward one another.

22. The apparatus of claim 13 wherein the first target and the second target are configured to be operated at separate speeds from one another.

23. A method of constructing a combined apparatus providing first and second streams of x-ray radiation comprising:
providing a first target in a first x-ray tube enclosure that is rotational about a first rotational axis, the first target having a first focal spot on a first face thereof to generate the first stream of x-ray radiation;
providing a first cathode in the first x-ray tube enclosure to emit a first beam of electrons toward the first target to generate the first stream of x-ray radiation;
providing a first rotating system adapted to rotate the first target about the first rotational axis, the first rotating system located in a position facing the first face of the first target;
providing a second target in a second x-ray tube enclosure that is rotational about a second rotational axis, the second target having a second focal spot on a second face thereof to generate the second stream of x-ray radiation, the second x-ray tube enclosure enclosing a volume that is separate from the first x-ray tube enclosure;

providing a second cathode in the second x-ray tube enclosure to emit a second beam of electrons toward the second target to generate the second stream of x-ray radiation;

providing a second rotating system adapted to rotate the second target about the second rotational axis, the second rotating system located in a position facing the second face of the second target; and placing the first x-ray tube in an abutting position proximate to the second x-ray tube such that the first face of the first target faces away from the second x-ray tube, and such that the second face of the second target faces away from the first x-ray tube;

wherein a path of the first beam of electrons and a path of the second beam of electrons are directed in directions along axes that are opposite to one another.

* * * * *